US00PP34267P2

(12) United States Plant Patent
Smith

(10) Patent No.: US PP34,267 P2
(45) Date of Patent: May 24, 2022

(54) ***CHRYSANTHEMUM* PLANT NAMED 'CIFZ0087'**

(50) Latin Name: ***Chrysanthemum* x *morifolium***
Varietal Denomination: CIFZ0087

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/232,463

(22) Filed: Apr. 16, 2021

(51) Int. Cl.
*A01H 5/02* (2018.01)
*A01H 6/14* (2018.01)

(52) U.S. Cl.
USPC ..... Plt./296

(58) Field of Classification Search
USPC ..... Plt./286, 296
See application file for complete search history.

*Primary Examiner* — Susan McCormick Ewoldt
(74) *Attorney, Agent, or Firm* — Dale Skalla

(57) ABSTRACT

A new garden type *Chrysanthemum* plant named 'CIFZ0087' particularly distinguished by its medium size plant with semi-upright plant habit, a medium to large size daisy flower, orange-bronze flower color and a natural season response in early September.

1 Drawing Sheet

Figure 1:
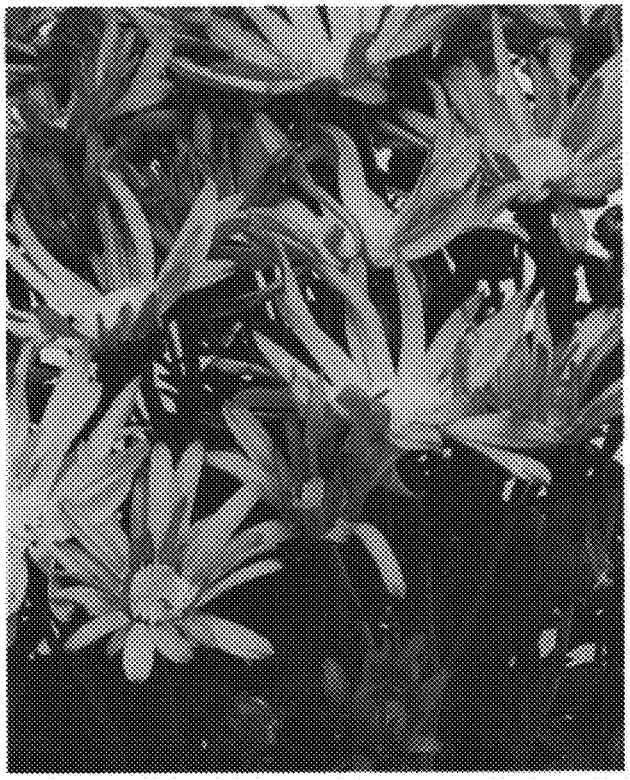

Latin name of the genus and species of the plant claimed: *Chrysanthemum* x *morifolium*.

Varietal denomination: 'CIFZ0087'.

BACKGROUND OF THE NEW PLANT

The present invention comprises a new *Chrysanthemum*, botanically known as *Chrysanthemum* x *morifolium*, and hereinafter referred to by the variety name 'CIFZ0087'.

'CIFZ0087' is a product of a planned breeding program. The new cultivar is a medium size plant with semi-upright plant habit, medium to large size daisy flowers, orange-bronze flower color and a natural season response early September.

'CIFZ0087' originated from a cross made in April 2016 in Enkhuizen, The Netherlands. Seeds were sown in June 2016 in Gilroy, Calif. and 'CIFZ0087' was selected from the resulting population on Oct. 24, 2016 in Alva, Fla.

The female parent was the variety 'Zanmuperfect', U.S. Plant Pat. No. 23,015.

TABLE 1

Characteristics of the female parent, compared to 'CIFZ0087':

| Trait | 'CIFZ0087' | 'Zanmuperfect' |
|---|---|---|
| Natural response: | 3/4 of a week faster | 3/4 of a week slower |
| Blackcloth response: | 1/2 week faster | 1/2 a week slower |
| Flower size: | Similar | Similar |
| Flower color: | Orange-bronze | Coral-pink |
| Flower type: | Daisy | Decorative |
| Plant size: | More height/similar width | Less height/similar width |
| Plant habit: | More upright | More flat mound |
| Flower longevity: | 20% longer | 20% shorter |

The male parent was 'Yobonnie', U.S. Plant Pat. No. 18,886.

TABLE 2

Characteristics of the male parent, compared to 'CIFZ0087':

| Trait | 'CIF0087' | 'Yobonnie' |
|---|---|---|
| Natural response - North: | Similar | Similar |
| Natural response - South: | 1 week faster | 1 week slower |
| Blackcloth response: | 1/2 week faster | 1/2 week slower |
| Flower size: | 1/4 in larger | 1/4 in smaller |
| Flower color: | Orange-bronze | Red |
| Flower type: | Similar | Similar |
| Plant size: | Similar | Similar |
| Plant habit: | More upright | More round mound |
| Flower longevity: | Slightly more | Slightly less |
| Plant strength: | Stronger | Weaker |

The first act of asexual reproduction of 'CIFZ0087' was accomplished when vegetative stem cuttings were propagated from the initial selection in January 2017 in Alva, Fla.

BRIEF SUMMARY OF INVENTION

Horticultural examination of plants grown from cuttings of the plant initiated in January 2017 and continuing thereafter, has demonstrated that the combination of characteristics as herein disclosed for 'CIFZ0087' are firmly fixed and are retained through successive generations of asexual reproduction.

'CIFZ0087' has not been observed under all possible environmental conditions. The phenotype may vary significantly with variations in environment such as temperature, light intensity and day length.

A Plant Breeder's Right for this cultivar has not yet been applied for. 'CIFZ0087' has not been made publicly available prior to the effective filing date of this application, notwithstanding any disclosure that may have been made less than one year prior to the effective filing date of this application by the inventor or another who obtained 'CIFZ0087' directly from the inventor.

The following traits have been repeatedly observed and are determined to be basic characteristics of the new variety.

The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0087' with colors being as true as possible with an illustration of this type.

Figure 2:
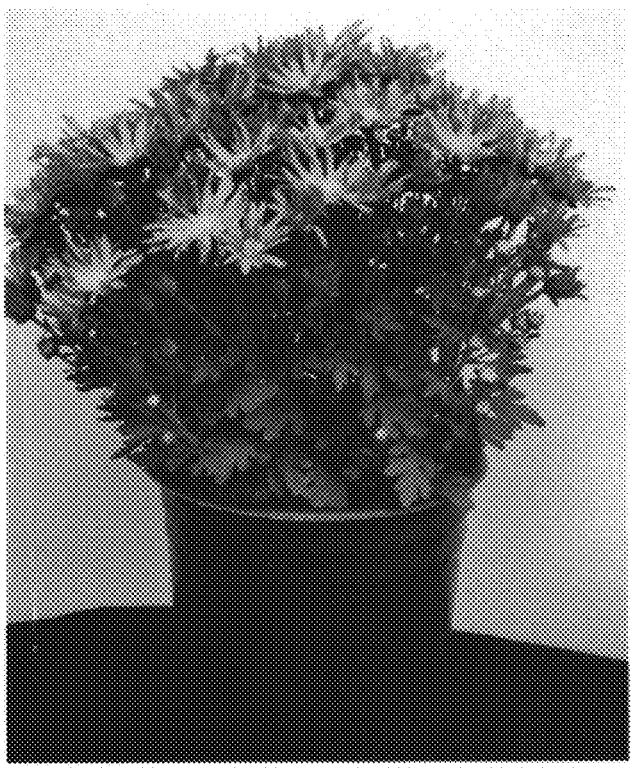

The photographic drawing shows in FIG. 1 a close view of flower of the new variety and in FIG. 2 a flowering plant from an indoor trial.

The aforementioned photographs: FIG. 1, as well as FIG. 2 were taken in September 2020, both showing a plant from the same blackcloth indoor trial in Gilroy, Calif.

These plants were about 10 weeks of age. One rooted cutting per pot had been planted in a one gallon pot, not pinched in week 24, and black clothed from week 25. Plants started flowering Mid-August.

DETAILED BOTANICAL DESCRIPTION

The measurements were taken in Gilroy, Calif. in September 2020 on the plants from the aforementioned trial.

Color references are made to The Royal Horticultural Society Colour Chart (R.H.S.) 2015.

TABLE 3

DIFFERENCES BETWEEN THE NEW VARIETY 'CIFZ0087' AND TWO MOST SIMILAR VARIETIES:

| Trait | 'CIFZ0087' | 'Yomichelle', U.S. Plant Pat. No. 17,439 |
|---|---|---|
| Natural response: | Similar | Similar |
| Blackcloth response: | Bit faster | Bit slower |
| Flower size: | Bit larger | Bit smaller |
| Flower color: | Orange-bronze | Yellow |
| Flower type: | Similar | Similar |
| Plant size: | Larger | Smaller |
| Plant habit: | More upright | Very round |
| Flower longevity: | Similar | Similar |
| Flowering uniformity: | Less uniform flowering | More uniform flowering |

TABLE 4

| Trait | 'CIFZ0087' | 'Mika Orange', U.S. Plant Pat. No. PP23,275 |
|---|---|---|
| Natural response: | 1/2 week slower | 1/2 week faster |
| Blackcloth response: | Similar | Similar |
| Flower size: | Slightly smaller | Slightly larger |
| Flower color: | Similar | Similar |
| Flower type: | Daisy with less ray florets | Duplex with more ray florets |
| Plant size: | Larger | Smaller |
| Plant habit: | Similar | Similar |
| Flower longevity: | Slightly more | Slightly less |

Plant:

*Form, growth and habit.*—Herbaceous garden-type, stems Upright and outwardly spreading, freely branching, strong and moderately vigorous growth habit.

*Plant height* (*above soil*).—20-22 cm.

*Plant height* (*inflorescence included*).—22-24 cm.

*Plant width.*—28 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137A.

*Immature leaf, color lower surface.*—RHS 137C.

*Mature leaf, color, upper surface.*—RHS NN137A.

*Mature leaf, color lower surface.*—RHS NN137C.

*Length.*—5.7 cm.

*Width.*—3.0 cm.

*Shape.*—Ovate, with distinct lobes.

*Base shape.*—Attenuate.

*Apex shape.*—Mucronate.

*Margin.*—5-lobed (palmate), edge dentate.

*Number of margin indentations.*—Medium.

*Depth of margin indentations.*—Medium-deep.

*Leaf length terminal lobe relative to total leaf length.*—Medium.

*Leaf depth lower lateral sinus.*—Deep.

*Texture, upper surface.*—Bifid hairs.

*Texture, lower surface.*—Bifid hairs.

*Color of veins, upper surface.*—RHS 138B.

*Color of veins, lower surface.*—RHS 138A.

*Pattern of veining.*—Palmate.

*Petiole color.*—RHS 137A.

*Petiole Length.*—1.0 cm.

*Diameter.*—0.2 cm.

*Texture.*—Bifid hairs.

*Presence of stipules.*—Yes.

*If present, size of stipules.*—Small.

Stem:

*Quantity of main branches per plant.*—4-5.

*Color of stem.*—RHS 138A.

*Length of stem.*—18.0 cm.

*Diameter.*—0.6 cm.

*Length of internodes.*—2.0 cm.

*Texture.*—Bifid hairs.

*Color of peduncle.*—RHS 138A.

*Length of peduncle.*—4.5 cm.

*Peduncle diameter.*—0.2 cm.

*Texture.*—Bifid hairs.

Inflorescence:

*Type.*—Compositae, solitary, daisy-type inflorescences borne terminally above foliage, ligulate ray florets arranged at the margin on a capitulum giving a single flower.

*Quantity of short days to flowering* (*response time*).—Approximately 6 weeks.

*Quantity of inflorescences per plant.*—110-120 with many small buds developing.

*Lastingness of individual blooms on the plant.*—About five weeks from first color.

*Fragrance.*—Slightly spicy.

Bud (when showing color):

*Color.*—RHS 8C.

*Length.*—0.5 cm.

*Width.*—0.8 cm.

*Shape.*—Oblate.

Immature inflorescence (at moment of opening):
*Diameter.*—1.3-1.5 cm.
*Color of ray florets, upper surface.*—RHS N163A.
*Color of ray florets, lower surface.*—RHS 163A with RHS N163A overtone.
Mature inflorescence:
*Diameter.*—4.5 cm.
*Depth.*—1.2 cm.
*Total diameter of disc.*—0.7 cm.
*Receptacle color.*—RHS NN137A.
*Receptacle height.*—0.5 cm.
*Receptacle diameter.*—1.0 cm.
*Length of corolla tube.*—Medium.
Ray florets:
*Average quantity of florets.*—30-40 in two whorls.
*Color of florets, upper surface.*—RHS 163B; 163A at apex.
*Color lower surface.*—RHS 163A.
*Length.*—1.5 cm.
*Width/diameter.*—0.4 cm.
*Shape.*—Elliptical.
*Apex shape.*—Mostly obtuse and dentate.
*Base shape.*—Tube.
*Margin.*—Entire. Small incisions may be present at tip.
*Margin.*—Type of rolling moderately involute.
*Texture, upper surface.*—Papillate.
*Lower surface.*—Papillate.
*Ribs present.*—Yes.
*Number of keels.*—2.
*Profile at widest point.*—Moderately convex.
*Longitudinal axis shape.*—Reflexing.
Disc florets:
*Number of disk florets.*—Up to 132.
*Width.*—Up to 0.2 cm.
*Length.*—1.5 cm.
*Colour.*—RHS 15A; 144B at base.
Inflorescence (at moment of senescence):
*Color of ray florets, upper surface.*—RHS 16B.
*Color of ray florets, lower surface.*—RHS 16B with fading rays of RHS 28B.
Phyllaries:
*Quantity.*—20.
*Color, upper surface.*—RHS NN137A.
*Color, lower surface.*—RHS 137A.
*Length.*—0.6 cm.
*Width.*—0.1-0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.
Reproductive organs:
*Pistil.*—One.
*Length.*—0.5 cm.
*Style color.*—RHS 150C.
*Style length.*—0.3 cm.
*Stigma color.*—RHS 15A.
*Stigma shape.*—Bi-parted.
*Ovary color.*—RHS 145C.
*Ovary length.*—0.2 cm.
*Ovary width.*—0.1 cm.
Androecium:
*Stamens.*—1, found on only disc florets.
*Color of filaments.*—RHS 15B.
*Length filaments.*—0.2 cm.
*Anther color.*—RHS 13A.
*Anther length.*—0.2 cm.
*Anther shape.*—Oval to club shaped.
*Color of pollen.*—RHS 13A.
*Pollen amount.*—Moderate.
*Fertility/seed set.*—Has not been determined to date.
*Disease/pest resistance.*—Has not been determined to date.
*Hardiness.*—Has not been determined to date.

What is claimed is:

1. A new and distinct variety of *Chrysanthemum* plant named 'CIFZ0087' substantially as illustrated and described herein.

* * * * *